United States Patent
Altounian

(10) Patent No.: US 9,414,899 B2
(45) Date of Patent: Aug. 16, 2016

(54) SYSTEM AND METHOD FOR SALIVA REPLENISHMENT AND CONTROL

(76) Inventor: Jennifer Rebecca Altounian, White Lake, MI (US)

(*) Notice: Subject to any disclaimer, the term of this patent is extended or adjusted under 35 U.S.C. 154(b) by 504 days.

(21) Appl. No.: 13/560,336

(22) Filed: Jul. 27, 2012

(65) Prior Publication Data
US 2013/0025607 A1 Jan. 31, 2013

Related U.S. Application Data

(60) Provisional application No. 61/512,440, filed on Jul. 28, 2011.

(51) Int. Cl.
*A61C 19/06* (2006.01)
*A61J 7/00* (2006.01)

(52) U.S. Cl.
CPC ............ *A61C 19/063* (2013.01); *A61J 7/0015* (2013.01); *A61J 7/0092* (2013.01)

(58) Field of Classification Search
CPC ...................................................... A63B 71/085
USPC .......... 128/861, 859, 857, 846, 860; 433/6, 2, 433/84, 88, 80, 25, 100, 120, 91, 92, 95; 601/1, 84, 154, 160, 162, 163–165
See application file for complete search history.

(56) References Cited

U.S. PATENT DOCUMENTS

| | | | |
|---|---|---|---|
| 522,842 A | 7/1894 | Lawshe | |
| 1,986,751 A | 1/1935 | Robinson | |
| 2,161,151 A | 6/1939 | Freedman | |
| 2,504,557 A | 4/1950 | Lumian | |
| 2,957,476 A * | 10/1960 | Freeman | 433/88 |
| 3,379,192 A * | 4/1968 | Warren, Jr. | 601/164 |
| 3,504,666 A * | 4/1970 | Vireno | A61C 17/0211 601/164 |
| 3,516,402 A * | 6/1970 | Toth | A61C 17/0211 601/164 |
| 3,731,675 A * | 5/1973 | Kelly | 601/164 |
| 3,834,226 A | 9/1974 | Pecorella et al. | |
| 4,164,940 A * | 8/1979 | Quinby | 601/164 |
| 4,299,568 A | 11/1981 | Crowley | |
| 4,560,351 A * | 12/1985 | Osborne | A61C 19/08 433/215 |
| 4,764,115 A | 8/1988 | Willits et al. | |
| 5,057,077 A | 10/1991 | Turner et al. | |
| 5,083,919 A * | 1/1992 | Quach | A61C 7/00 433/24 |
| 5,104,315 A * | 4/1992 | McKinley | A61C 17/0211 433/216 |
| 5,364,269 A | 11/1994 | Willits et al. | |
| 5,484,405 A | 1/1996 | Edstrom, Sr. | |
| 5,509,801 A * | 4/1996 | Nicholson | 433/80 |
| 5,512,045 A | 4/1996 | Gurchumelidze | |

(Continued)

OTHER PUBLICATIONS

Devilbiss Homecare Suction Unit with Battery, http://healthproductsforyou.com/p-3773-devilbiss-homecare-suction-unit-with-battery.ht . . . , 2 pgs, 2013.

(Continued)

*Primary Examiner* — Nicholas Woodall
*Assistant Examiner* — Tarla Patel
(74) *Attorney, Agent, or Firm* — Harness, Dickey & Pierce, P.L.C.

(57) ABSTRACT

Disclosed is a system for providing artificial saliva. The system can include the mouthpiece, a portable supply unit, and a stationary supply unit. The portable supply unit can be adapted to be carried by a user. The portable supply unit can include a first fluid system, a first interface module, and a first control module. The first fluid system can be adapted to fluidly couple to the mouthpiece.

17 Claims, 13 Drawing Sheets

(56) References Cited

U.S. PATENT DOCUMENTS

| | | | |
|---|---|---|---|
| 5,529,214 | A | 6/1996 | Lasonde et al. |
| 5,749,898 | A | 5/1998 | Schulze et al. |
| 5,984,145 | A | 11/1999 | McAllister |
| 6,000,395 | A | 12/1999 | Brown |
| 6,267,596 | B1 | 7/2001 | Kalfas |
| 6,283,344 | B1 | 9/2001 | Bradley |
| 6,893,259 | B1 | 5/2005 | Reizenson |
| 6,896,516 | B2 | 5/2005 | Lin et al. |
| 7,118,377 | B2 * | 10/2006 | Inoue ................... A61C 19/063 433/80 |
| 8,122,889 | B2 * | 2/2012 | Vaska et al. ................... 128/848 |
| 8,371,853 | B2 * | 2/2013 | Levine .......................... 433/215 |
| 8,464,709 | B2 * | 6/2013 | Wedemeyer ............. 128/200.26 |
| 8,684,956 | B2 * | 4/2014 | McDonough ...... A61C 17/0211 433/216 |
| 2003/0091210 | A1 | 5/2003 | Baskerville |
| 2005/0064370 | A1 * | 3/2005 | Duret ................... A61C 19/066 433/215 |
| 2007/0204867 | A1 | 9/2007 | Kennedy, Jr. et al. |
| 2008/0171303 | A1 | 7/2008 | Roberts et al. |
| 2009/0208898 | A1 | 8/2009 | Kaplan |
| 2012/0199135 | A1 * | 8/2012 | Podmore et al. ............... 128/848 |

OTHER PUBLICATIONS

Invacare Aspirator, http://www.invacare.com/cgi-bin/imhqprd/inv_catalog/prod_cat_detail.jsp?prodID=IRC1135, 2 pgs, 2013.

IsoliteSystems, http://www.isolitesystems.com/explore-dental-isolation-systems/select-the-right-system-for-you-/isolite, 2 pgs, 2013.

Allied Healthcare Products Inc., DC Portable Aspirator Operation/Service Manual, Gomco G180 Portable Suction Device, https://www.alliedhpi.com/images/zs168-507-001_h.pdf, 13 pgs, 2013.

* cited by examiner

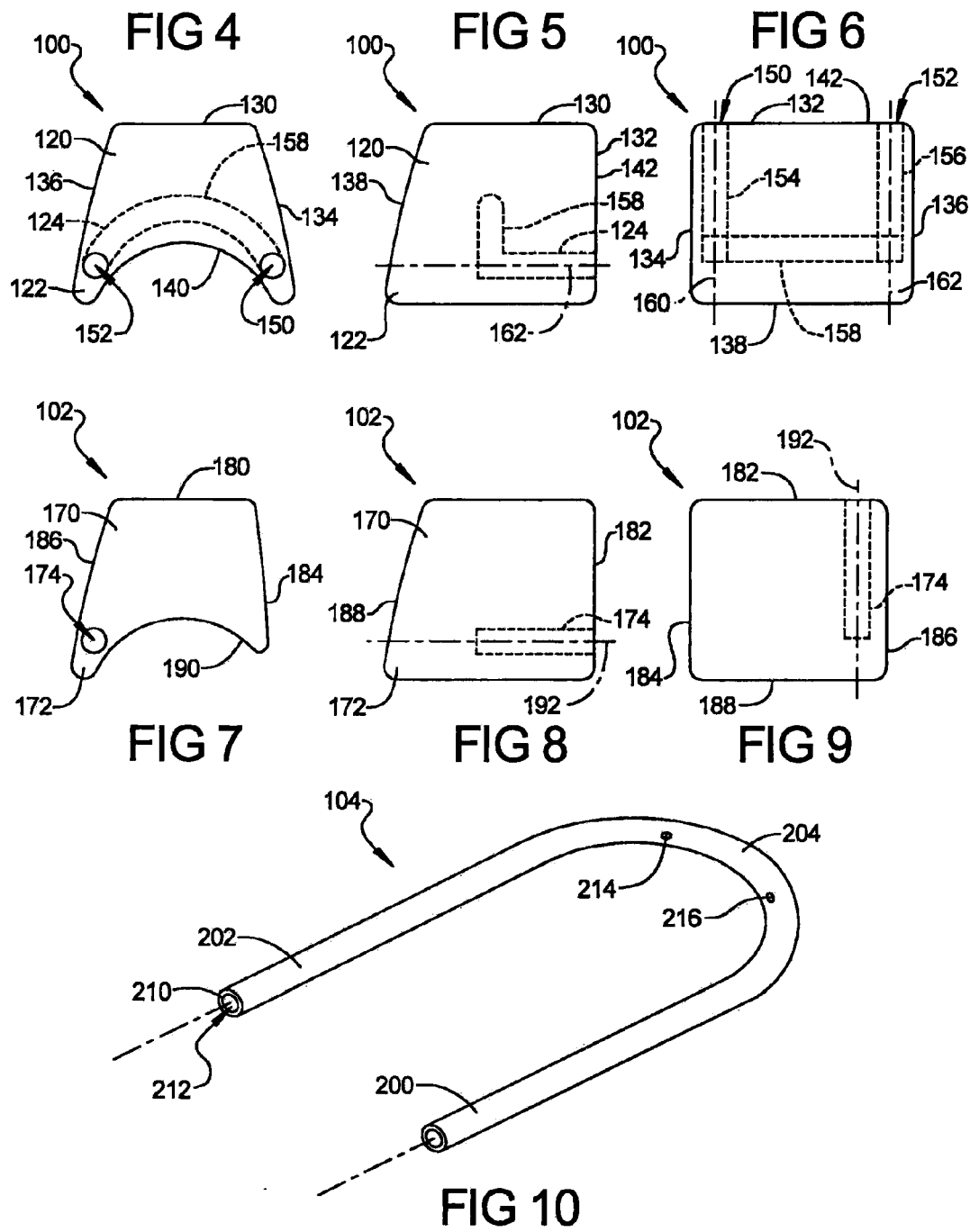

SYSTEM AND METHOD FOR SALIVA REPLENISHMENT AND CONTROL

CROSS-REFERENCE TO RELATED APPLICATIONS

This application claims the benefit of U.S. Provisional Application No. 61/512,440, filed on Jul. 28, 2011. The entire disclosure of the above application is incorporated herein by reference.

FIELD

The present disclosure relates to systems and methods for saliva replenishment and control and, more particularly, to mouthpieces and fluid delivery systems.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Saliva production is important to several biological functions including swallowing, digestion, and oral hygiene. For example, enzymes in saliva aid digestion. As another example, saliva hydrates the mouth and throat, aiding swallowing and promoting oral hygiene. Salivary glands may become impaired and/or damaged due to accident, trauma, illness, disease, and/or medical treatments including surgery, medications, radiation therapy, and chemotherapy treatments. In some cases, the accident, trauma, illness, disease, or medical treatment can seriously impair or permanently damage the salivary glands and, as a consequence, render normal salivary production impossible.

As one example, a condition referred to as Xerostomia in the medical community afflicts millions of people worldwide. Xerostomia is used to refer to a condition in which saliva production is impaired or absent. Xerostomia can be caused by various diseases such as Sjögren's syndrome, human immunodeficiency virus (HIV), Alzheimer's disease, diabetes, cystic fibrosis, lupus, and rheumatoid arthritis. As another example, people undergoing cancer treatments such as radiation therapy and chemotherapy to the head and neck often experience a loss in saliva production, and the loss can be permanent. Medications may also diminish saliva production. Saliva production may also diminish as an individual ages and can become problematic at advanced ages.

Several problems can arise in an individual whose saliva production is compromised. Without the ability to produce saliva, an individual may not produce the enzymes necessary to properly digest food. Tooth decay, painful sores in the mouth, problems swallowing, and the inability to eat and speak can arise and can cause other significant health issues. For example, psychological stress and/or other problems can develop. At a minimum, an individual's quality of life can be negatively impacted.

Accordingly, there is a need for devices that can be used to replenish saliva and control saliva production, as well as provide a more convenient way to deliver medications to patients. Several devices have been developed. However, these devices can be improved upon. Specifically, the comfort, versatility, operation, and appearance can be improved upon. Through such improvements, patient compliance with therapies directed to saliva production and other health issues can be improved along with the patient's quality of life. Additionally, such improvements can make certain treatments such as cancer treatments more tolerable and provide for a more stable overall health.

SUMMARY

In one form, the present disclosure provides a mouthpiece. The mouthpiece can include a first anchoring member, a second anchoring member, a first tube, and a second tube. The first anchoring member can be adapted to engage a lower dental arch adjacent a first tooth on a first side of a mouth. The first anchoring member can include a first passage extending between a vestibule on the first side of the mouth and a mouth cavity proper. The second anchoring member can be adapted to engage the lower dental arch adjacent a second tooth on a second side of the mouth. The first tube can extend within the mouth cavity proper from the first anchoring member to the second anchoring member adjacent to an inner gum line. The first tube can include a first end fluidly coupled to the first passage, a second end opposite the first end attached to the second anchoring member, and an aperture extending through a wall of the first tube into the mouth cavity proper. The second tube can extend within the vestibule on the first side of the mouth adjacent to an outer gum line. The second tube can include a first end fluidly coupled to the first passage and a second end extending outside of the mouth.

In various features, the second anchoring member can include a second passage extending between the vestibule on the second side of the mouth and the mouth cavity proper. In a related feature, the second end of the first tube can be fluidly coupled to the second passage. In another related feature, the mouthpiece can further include a third tube extending within the vestibule on the second side of the mouth adjacent to the outer gum line. The third tube can include a first end fluidly coupled to the second passage and a second end extending outside of the mouth.

The present disclosure also provides a system that can include the mouthpiece, a portable supply unit, and a stationary supply unit. The portable supply unit can be adapted to be carried by a user. The portable supply unit can include a first fluid system, a first interface module, and a first control module. The first fluid system can be adapted to fluidly couple to the mouthpiece. The first fluid system can supply saliva replenishment fluid to the mouth via the mouthpiece and/or remove fluid from the mouth via the mouthpiece based on first operational settings. The first interface module can receive a first input and can communicate the first operational settings with the stationary supply unit. The first control module can selectively adjust the first operational settings based on the first input and second operational settings communicated by the stationary supply unit. The stationary supply unit can include a second fluid system, a second interface module, and a second control module. The second fluid system can be adapted to fluidly couple to the mouthpiece. The second fluid system can supply saliva replenishment fluid to the mouth via the mouthpiece and/or remove fluid from the mouth via the mouthpiece based on the second operational settings. The second interface module can receive a second input and can communicate the second operational settings with the portable supply unit. The second control module can selectively adjust the second operational settings based on the second input and the first operational settings.

In another form, the present disclosure provides methods related to a mouthpiece and a system according to the present disclosure.

Further areas of applicability of the present disclosure will become apparent from the detailed description provided hereinafter. It should be understood that the detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein:

FIG. 4 is a front elevation view illustrating an exemplary first anchoring member of the mouthpiece shown in FIG. 1;

FIG. 5 is a side elevation view illustrating the first anchoring member of the mouthpiece shown in FIG. 1;

FIG. 6 is a top elevation view illustrating the first anchoring member of the mouthpiece shown in FIG. 1;

FIG. 7 is a front elevation view illustrating an exemplary second anchoring member of the mouthpiece shown in FIG. 1;

FIG. 8 is a side elevation view illustrating the second anchoring member of the mouthpiece shown in FIG. 1;

FIG. 9 is a top elevation view illustrating the second anchoring member of the mouthpiece shown in FIG. 1;

FIG. 10 is a perspective view illustrating an exemplary first tubular member of the mouthpiece shown in FIG. 1;

DETAILED DESCRIPTION

Figure 1:
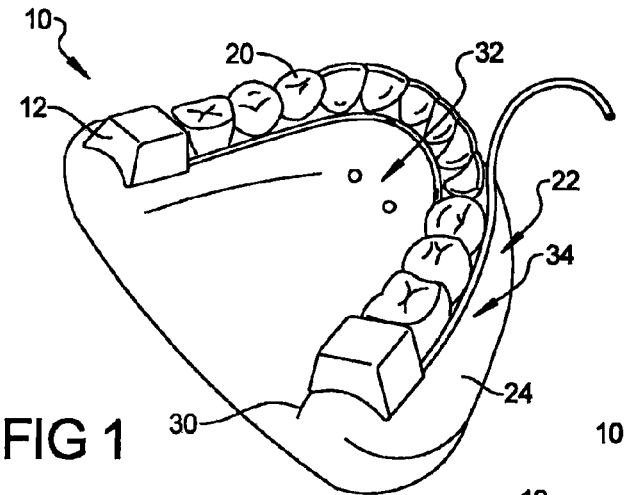
FIG. 1 is an environmental perspective view of a lower portion of a mouth illustrating a first exemplary mouthpiece attached to the mouth according to the present disclosure.

The following description is merely illustrative in nature and is in no way intended to limit the disclosure, its application, or uses. For purposes of clarity, the same reference numbers will be used in the drawings to identify similar elements. As used herein, the phrase at least one of A, B, and C should be construed to mean a logical (A or B or C), using a non-exclusive logical or. It should be understood that steps within a method may be executed in different order without altering the principles of the present disclosure.

As used herein, the term module may refer to, be part of, or include an Application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above, such as in a system-on-chip. The term module may include memory (shared, dedicated, or group) that stores code executed by the processor.

The term code, as used above, may include software, firmware, and/or microcode, and may refer to programs, routines, functions, classes, and/or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors or a group of execution engines. For example, multiple cores and/or multiple threads of a processor may be considered to be execution engines. In various implementations, execution engines may be grouped across a processor, across multiple processors, and across processors in multiple locations, such as multiple servers in a parallel processing arrangement. In addition, some or all code from a single module may be stored using a group of memories.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

The present disclosure provides a mouthpiece that can be attached to a lower portion of a mouth and can be used to replenish and/or control saliva in a patient or user. The user can be a male or female and can be an adult or child. The mouthpiece can be used during treatment of temporary conditions such as a temporary loss of swallowing capability due to an accident or trauma, or chronic conditions and diseases such as Xerostomia and cancers affecting salivary function. The mouthpiece can be used to supply and/or remove fluid from the mouth. The mouthpiece is designed so that it can be relatively inconspicuous and minimally intrusive, and can be continuously worn for prolonged periods, for example days and weeks. The mouthpiece is further designed so that it can be used to supply a saliva replenishment fluid in a manner that mimics a normal saliva flow within the mouth. By incorporating such design features, the mouthpiece can be comfortably used without compromising chewing, eating, speaking, and sleeping, and can promote patient compliance with therapies dependent on the use of the mouthpiece.

In various aspects, the mouthpiece can be individually sized and made to fit a particular user. The mouthpiece can have a modular construction that further enables components of the mouthpiece as produced to be altered and custom fit to a particular patient. The modular construction can also enable one or more components of the mouthpiece to be individually replaced without the need for another complete replacement mouthpiece. The components can be individually replaced to maintain a desired sanitary condition of the mouthpiece.

Figure 2:
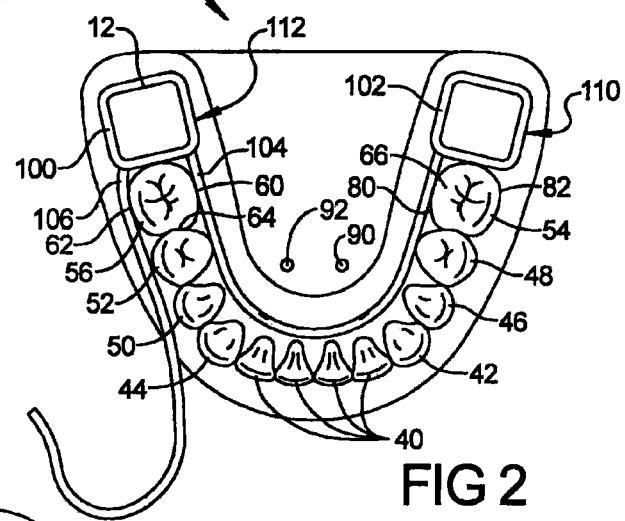
FIG. 2 is an environmental top elevation view of the lower portion of the mouth illustrating the mouthpiece shown in FIG. 1.
Figure 3:
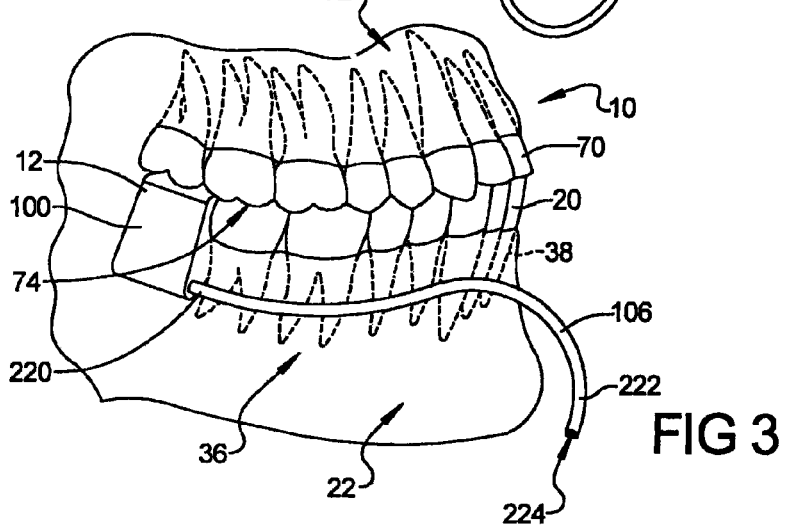
FIG. 3 is an environmental side elevation view of the mouth illustrating the mouthpiece shown in FIG. 1.

With particular reference to FIGS. 1-3, environmental views of a lower portion of a mouth 10 illustrate an exemplary mouthpiece 12 according to the present disclosure. The mouth 10 includes lower teeth 20 anchored in a lower jaw bone 22 by gingiva or gum 24. The mouth 10 includes a lower alveolar or dental arch 30 separating a mouth cavity proper 32 and a vestibule 34. The lower dental arch 30 includes alveolar processes 36 that receive roots 38 of the lower teeth 20, the lower teeth 20, and portions of the gum 24 covering the alveolar processes 36 and surrounding the lower teeth 20. The lower teeth 20 can include up to twelve deciduous teeth in a child and up to 16 permanent teeth in an adult. For exemplary purposes, the lower teeth 20 presented include twelve teeth: four incisors 40, two canines 42, 44, four premolars 46, 48, 50, 52, and two molars 54, 56. The lower teeth 20 include lingual surfaces 60 facing the mouth cavity proper 32 and a tongue (not shown), labial or buccal surfaces 62 facing the vestibule 34 and a cheek (not shown) and lips (not shown), and surfaces of contact 64 between adjoining teeth. The lower teeth 20 further include crowns 66 facing upper teeth 70 of an upper jaw bone 72 and defining a lower bite surface or plane 74. Together, the lower teeth 20 and the gum 24 define an inner gum line 80 and an outer gum line 82. Openings of a submandibular duct within the mouth cavity proper 32, which may be referred to as the Wharton's duct, are illustrated by openings 90, 92.

The mouthpiece 12 can include a first anchoring member 100, a second anchoring member 102, a first tubular member 104, and a second tubular member 106. The first and second anchoring members 100 and 102 can attach to opposite sides of the lower dental arch 30 in spaces 110 and 112 adjacent the molars 54 and 56 where second and third molars once resided. In various aspects, the spaces 110 and 112 can be spaces behind rearmost teeth, or in a space where one or more molars once resided such as in the present example. As another example, the spaces 110, 112 can be spaces located in a space between two teeth where one or more teeth once resided. The spaces 110, 112 can be spaces created by extracting one or more of the lower teeth 20 to make room for the first and second anchoring members 100, 102. The spaces 110, 112 can be located in an area of the mouth 10 least affected by the bone loss associated with certain illnesses and treatments. The first and second anchoring members 100 and 102 can be sized to fit within the spaces 110, 112 and not protrude above the bite plane 74. The first and second anchoring members 100 and 102 can be generally solid structures and can have various shapes adapted to fit within the spaces 110 and 112 adjacent to the molars 54 and 56 and adjoining teeth of the upper teeth 70.

With additional reference to FIGS. 4-6, the first anchoring member 100 can include a crown 120, an anchoring portion 122, and a passage 124. The crown 120 extends from the anchoring portion 122 and can be integral with the anchoring portion 122 as a single piece. The crown 120 can have a generally tapered polyhedral shape as illustrated, or can have a contoured shape resembling a natural tooth that may otherwise reside in the space 110. The crown 120 can include a superior or top surface 130, and an anterior or front surface 132, lateral or side surfaces 134, 136, and a posterior or back surface 138 extending from the top surface 130 to the anchoring portion 122.

The top surface 130 can be adapted and disposed to engage one or more of the upper teeth 70. The top surface 130 can be generally flat as shown and, optionally, can include a portion complementary to adjoining surfaces of the upper teeth 70.

The front surface 132 can be adapted and disposed to engage one or more of the surface of contact 64, the lingual surface 60, and the buccal surface 62 of the molar 56. The front surface 132 can be further disposed to allow one end of the passage 124 to exit the front surface 132 adjacent the lingual surface 60 of the molar 56 and an opposite end of the passage 124 to exit the front surface 132 adjacent the buccal surface 62 of the molar 56. In this way, the front surface 132 can be disposed to allow the first tubular member 104 to extend from the front surface 132 adjacent the lingual surface 60 of the molar 56, and the second tubular member 106 to extend from the front surface 132 adjacent the buccal surface 62 of the molar 56. The front surface 132 can be generally flat as illustrated by the present example and, optionally, can include a portion complementary to the adjoining surface of contact 64 of the molar 56. In this way, the front surface can engage and thereby resist relative movement between the first anchoring member 100 and the molar 56.

The side surfaces 134 and 136 extend from the top surface 130 to the anchoring portion 122 and can be smooth surfaces adapted to engage the tongue and the cheek respectively in a pleasant or comfortable manner. The side surfaces 134 and 136 and the back surface 138 can taper outward from the top surface 130 so that an upper portion of the crown 120 is smaller than a lower portion of the crown 120 and the anchoring portion 122 as illustrated by the present example.

The anchoring portion 122 can include an inferior or gum engaging surface 140 that attaches to the lower dental arch 30 and supports the first anchoring member 100. The gum engaging surface 140 can be generally concave and, optionally, can include portions complementary to portions of the gum 24 defining the space 110. The anchoring portion 122 can engage sides of the lower dental arch 30 facing the mouth cavity proper 32 and the vestibule 34 and, in this way, can resist relative movement between the first anchoring member 100 and the lower dental arch 30 in the medial-lateral direction.

The passage 124 can extend through the first anchoring member 100 and can provide fluid communication between the first tubular member 104 disposed in the mouth cavity proper 32 and the second tubular member 106 disposed in the vestibule 34. The passage 124 can be sized and configured to allow a desired flow rate of fluid between the first and second tubular members 104 and 106. The passage 124 can extend from an aperture 150 disposed in the vestibule 34 to an aperture 152 disposed in the mouth cavity proper 32. The passage 124 can extend through the front surface 132 as illustrated by the present example or, optionally, can extend through one or more of the top surface 130, the side surfaces 134, 136 and the back surface 138.

The passage 124 can include a first leg 154, a second leg 156, and a third leg 158. The first leg 154 can extend through the front surface 132 towards the back surface 138 along an axis 160. The first leg 154 can be adapted to receive an end of the first tubular member 104 in a press-fit arrangement and thereby releasably couple the first anchoring member 100 and the first tubular member 104. The first leg 154 can be sized to receive the first anchoring member 100 at various depths of insertion. The axis 160 can be oriented substantially parallel to the inner gum line 80 or, optionally, disposed on an angle downward towards the openings 90, 92 of the submandibular duct. The second leg 156 can extend through the front surface 142 towards the back surface 138 along an axis 162. The second leg 156 can be adapted to receive an end of the second tubular member 106 in a press-fit and thereby couple the first anchoring member 100 and the second tubular member 106. The second leg 156 can be sized to receive and couple the first tubular member 104 at various depths of insertion. The axis 162 can be oriented substantially parallel to the axis 160 or, optionally, can be oriented at an angle towards a corner of the opening of the mouth 10. The third leg 158 can extend from the first leg 154 to the second leg 156.

With additional reference to FIGS. 7-9, the second anchoring member 102 can include a crown 170, an anchoring portion 172, and a coupling in the form of a blind bore 174. The crown 170 extends from the anchoring portion 172 and can be integral with the anchoring portion 122 as a single piece as illustrated by the present example. The crown 170 can have a generally tapered polyhedral shape similar to that of the crown 120 of the first anchoring member 100, or can have a contoured shape resembling a natural tooth that once resided in the space 112. The crown 170 can include a superior or top surface 180, and an anterior or front surface 182, lateral or side surfaces 184, 186, and a posterior or back surface 188 extending from the top surface 180 to the anchoring portion 172. The top surface 180 can be adapted and disposed to engage one or more of the upper teeth 70. The top surface 180 can be generally flat as shown and, optionally, can include a portion complementary to adjoining surfaces of the upper teeth 70.

The front surface 182 can be adapted and disposed to engage one or more of the surface of contact 64, the lingual surface 60, and the buccal surface 62 of the molar 54. The front surface 182 can further be disposed to allow the open end of the bore 174 to exit the front surface 182 adjacent the lingual surface 60 of the molar 54. In this way, the front surface 182 can be disposed to allow the first tubular member 104 to extend from the front surface 182 adjacent the lingual surface 60 of the molar 54. The front surface 182 can be generally flat as illustrated. The front surface 182 can include a portion complementary to the adjoining surface of contact 64 of the molar 54 that engages the molar 54 and thereby resists relative movement between the second anchoring member 102 and the molar 54.

The side surfaces 184, 186 can be smooth surfaces adapted to engage the tongue and the cheek, respectively, in a pleasant or comfortable manner. The side surfaces 184, 186 and the back surface 188 can taper outward from the top surface 180 so that an upper portion of the crown 170 is smaller than a lower portion of the crown 170 and the anchoring portion 172 as illustrated by the present example.

The anchoring portion 172 can include an inferior or gum engaging surface 190 that attaches to the lower dental arch 30 and supports the second anchoring member 102. The gum engaging surface 140 can be generally concave and optionally can include portions complementary to portions of the gum 24 defining the space 112. The anchoring portion 172 can engage sides of the lower dental arch 30 facing the mouth cavity proper 32 and the vestibule 34 and, in this way, can resist relative movement between the second anchoring member 102 and the lower dental arch 30 in the medial-lateral direction.

The bore 174 can receive an end of the first tubular member 104 in a press-fit arrangement and, in this way, can couple the first tubular member 104 to the second anchoring member 102. The bore 174 can be sized to receive and couple the first tubular member 104 at various depths of insertion and can seal an end of the first tubular member 104. The bore 174 can extend partially through the second anchoring member 102 along an axis 192. The axis 192 can be oriented substantially parallel to the inner gum line 80 or, optionally, disposed at an angle downward towards the openings 90, 92 of the submandibular duct.

In various aspects, the first and second anchoring members 100 and 102 can be made in a mirror image to that described above. In this way, the mouthpiece 12 may be configured so that the tubular member 104 exits the mouth 10 on the left side of the user.

In various aspects, the first and second anchoring members 100 and 102 can be attached in any suitable manner. For example, a suitable adhesive such as an adhesive that adheres dentures to gum may be used. In various aspects, the first and second anchoring members 100 and 102 can be attached in a semi-permanent manner using a bone fastener. Semi-permanent fastening may be desired for users who expect to use the mouthpiece 12 over a prolonged period and who are unable and/or unwilling to detach and re-attach the mouthpiece 12 as may otherwise be required. In other aspects, the first and second anchoring members 100 and 102 can be positioned against the lower dental arch 30 and attached to an adjoining tooth.

In various aspects, the first and second anchoring members 100 and 102 can be made from any suitable dental material. Suitable dental materials include, but are not limited to, biocompatible polymers such as acrylic materials, and metals such as titanium.

In various aspects, the first and second anchoring members can be off-the-shelf components, semi-custom components, or custom components. As used herein, off-the-shelf components can refer to components made without features based on a particular user. Semi-custom components can refer to components made in advance that include a majority of predetermined features not based on a particular user and at least one feature based on a particular user. Custom components can refer to components specifically made for a particular user. The patient-specific features of a semi-custom component and a custom component can be formed based on a particular user's lower dental arch and surrounding mouth anatomy using various techniques such as dental impressioning techniques.

In one example of off-the-shelf components, the first and second anchoring members 100 and 102 can be selected from a set of components of various sizes made in advance.

In one example of semi-custom components, the crowns 120, 170 of the first and second anchoring members 100 and 102 can be made to predetermined sizes and shapes that are not based on a particular user and the anchoring portions 122, 172 can be made from dental impressions made from a particular user.

In one example of custom components, the first and second anchoring members 100 and 102 can be made entirely from dental impressions made from a particular user. In this way, the crowns 120, 170 can be made to engage and closely match the upper teeth 70. In this way, the first and second anchoring members 100 and 102 can support the upper teeth 70 and can preserve a natural bite plane.

In various aspects, the passage 124 and the bore 174 can be molded in the first and second anchoring members 100 and 102. Alternately, one or more of the legs 154, 156, 158 of the passage 124 and the bore 174 can be formed by drilling into the first and second anchoring members 100 and 102. For example, the first and second legs 154 and 156 can be formed by drilling through the front surface 132. The third leg 158 can be formed by drilling a first passage through the side surface 134 and a second passage through the side surface 136 so that the first and second passages intersect. Plugs can be used to seal the apertures formed in the side surfaces 134, 136 during drilling.

With additional reference to FIG. 10, the first tubular member 104 can be a length of transparent flexible tubing. The tubing can be round tubing as illustrated by the present example or, alternatively, can have any other suitable cross-section. Transparent tubing can enable the first tubular member 104 to be more inconspicuous and can enable debris and other contaminants that may be present within the tubing to be more easily identified. The first tubular member 104 can be coupled to the first anchoring member 100 via the first leg 154 at a first end 200 and to the second anchoring member 102 via the bore 174 at a second end 202 opposite the first end 200. In various aspects, the first tubular member can be made by bending a length of straight flexible tubing or, optionally, can be made to have a desired pre-formed shape. The first tubular member 104 can extend between the first and second anchoring members 100 and 102 along or just below the inner gum line 80 as illustrated by the present example. For example, the first tubular member 104 can extend below the inner gum line 80 at the front of the mouth cavity proper 32 so that an arched portion 204 is disposed in a natural space between the gum 24 and a bottom of the tongue adjacent to the openings 90, 92 of the submandibular duct.

The first tubular member 104 can include a wall 210 defining a longitudinal passage 212, and one or more apertures extending through the wall 210. For example, two apertures 214, 216 can be provided. The apertures 214 and 216 can be disposed adjacent to, and to face towards, the openings 90 and 92, respectively, of the submandibular duct as illustrated by the present example. In this way, the apertures 214, 216 can supply fluid in the area of the openings 90, 92 and thereby enable the mouthpiece 12 to mimic the normal operation of the salivary gland and create a flow of fluid substantially similar to or mimicking a natural saliva flow. The longitudinal passage 212 and the apertures 214, 216 can be sized so that fluid can pass between the mouth cavity proper 32 and the passage 212. In various aspects, additional apertures can be provided to create the desired flow of fluid. Additional apertures can be provided at various locations to create the desired flow of fluid and/or facilitate the removal of fluid from the mouth. For example, additional apertures can be located adjacent excretory ducts other than the submandibular duct and/or other areas of the mouth cavity proper 32 where saliva tends to pool.

With particular reference again to FIGS. 1-6, the second tubular member 106 can be a length of transparent flexible tubing. The second tubular member 106 can be coupled to the first anchoring member 100 via the second leg 156 at a first end 220 and to a fluid system (e.g., fluid system 550, 600) located outside the mouth 10 at a second end 222 opposite the first end 220. The second tubular member 106 can include a longitudinal passage 224 sized so that fluid can pass between the mouth cavity proper 32 and the fluid system.

With continued reference to FIGS. 1-10, exemplary methods of fitting the mouthpiece 12 to a user according to the present disclosure will now be described. According to a first example, a method of fitting the mouthpiece to a user can include at least partially assembling the mouthpiece 12 prior to attaching the first anchoring member 100 and/or the second anchoring member 102 to the gum 24. More specifically, the method can include: (i) coupling the first tubular member 104 to the first anchoring member 100 by inserting the first end 200 within the first leg 154 of the passage 124 to a depth where the first end 200 engages the passage 124 in a press-fit arrangement, (ii) coupling the first tubular member 104 to the second anchoring member 102 by inserting the second end 202 within the bore 174 to a depth where the second end 202 engages the bore 174 in a press-fit arrangement, (iii) attaching at least one of the first anchoring member 100 and the second anchoring member to the lower dental arch 30 after coupling the first tubular member 104 according to (i) and (ii), (iv) attaching a remaining one of the first anchoring member 100 and the second anchoring member 102 to the lower dental arch 30, and (v) attaching the second tubular member 106 to the first anchoring member 100 by inserting the end 220 within the second leg 156 of the passage 124 to a depth where the end 220 engages the passage 124 in a press-fit arrangement. The first method can further include (vi) selecting a user, and (vii) adjusting a fit of the mouthpiece 12 to the user by adjusting the depth of the first tubular member 104 within one of the passage 124 and the bore 174.

According to a second example, a method of fitting the mouthpiece to a user can include coupling the first and second tubular members 104 and 106 to the first and second anchoring members 100 and 102 after attaching the first and second anchoring members 100 and 102 to the gum 24.

With continued reference to FIGS. 1-10, exemplary methods of using the mouthpiece 12 according to the present disclosure will now be described. According to a first method, the mouthpiece 12 can be coupled to a fluid delivery system and used to supply fluid to the mouth of a user whose saliva production is low. The method can include coupling the mouthpiece 12 to the fluid delivery system and supplying the fluid under pressure to the mouthpiece 12 via the second tubular member 106. Pressurized fluid can be received through the passage 224 and can pass through the passage 124 of the first anchoring member 100 and the passage 212 of the first tubular member 104. The fluid can exit the apertures 214, 216 into the mouth cavity proper 32 near the openings 90, 92 of the submandibular duct where natural saliva is be secreted.

According to a second method, the mouthpiece 12 can be coupled to a fluid removal system and used to remove excess fluid from the mouth of a user whose saliva production is too high or who cannot swallow properly. The method can include coupling the mouthpiece 12 to the fluid removal system and drawing fluid from within the mouth cavity proper 32 through the apertures 214, 216 under vacuum. Fluid drawn through the apertures 214, 216 can pass through the passage 212 of the first tubular member 104, the passage 124 of the first anchoring member 100, and the passage 224 in that order. The fluid can exit the passage 124 and can be collected in the fluid removal system.

In various aspects, the method can further include adjusting a depth of insertion of one or both the ends 200, 202 to adjust a fit of the first tubular member 104 within the mouth cavity proper 32 after attaching the first and second anchoring members 100 and 102. Adjustments can be made to relieve pressure at points of contact between the first tubular member 104 and the gum 24 and thereby provide a comfortable fit. In other aspects, the method can further include replacing the first tubular member 104 and/or the second tubular member 106 without detaching the first and second anchoring members 100 and 102. The first tubular member 104 can be replaced by removing the ends 200, 202 from passage 124, disposing the first tubular member 104, and coupling a replacement part to the first and second anchoring members 100 in a manner similar to that described for the first tubular member 104. The second tubular member 106 can be replaced by removing the first end 200 from the bore 174, disposing the second tubular member 106, and coupling a replacement part to the first anchoring member 100 in a manner similar to that described for the second tubular member 106.

In various aspects, the mouthpiece 12 can be worn while eating and can aid in the chewing and swallowing of food. For example, the mouthpiece 12 can be used to deliver a quantity of saliva replenishment fluid that assists chewing and swallowing. The mouthpiece can enable the saliva replenishment fluid to be delivered at intervals or continuously.

Figure 11:
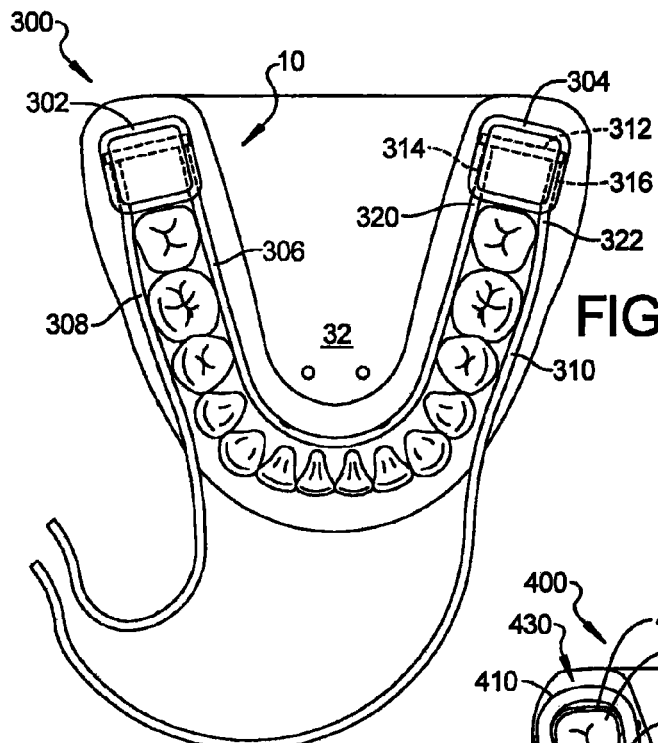
FIG. 11 is an environmental top elevation view of a lower portion of a mouth illustrating another exemplary mouthpiece according to the present disclosure.

With particular reference to FIG. 11, an environmental top elevation view illustrates another mouthpiece 300 for use with the mouth 10 according to the present disclosure. The mouthpiece 300 can include a first anchoring member 302, a second anchoring member 304, a first tubular member 306, a second tubular member 308, and a third tubular member 310. The first anchoring member 302, the first tubular member 306, and the second tubular member 308 can be substantially similar to the first anchoring member 100, the first tubular member 104, and the second tubular member 106, respectively.

The second anchoring member 304 can attach to the lower dental arch 30 in the space 112 and can engage the molar 56 in a substantially similar manner as the second anchoring member 102. The second anchoring member 304 can include a passage 312 that can couple to, and that can provide fluid communication between, the first and third tubular members 306 and 310. The passage 312 can extend through the second anchoring member 304, and can couple to the first and third tubular members 306 and 310 in a manner similar to that of the passage 124. In particular, the passage 312 can include a first leg 314 and a second leg 316. The first leg 314 can receive an end 320 of the first tubular member 306 in a press-fit arrangement similar to that created between the first anchoring member 100 and the first tubular member 104. The second leg 316 can receive an end 322 of the third tubular member 310 in a press-fit arrangement similar to that created between the first anchoring member 100 and the second tubular member 106.

The mouthpiece 300 can include the feature that fluid can be supplied to the mouth cavity proper 32 and removed from the mouth cavity proper 32 through separate passages created by the mouthpiece 300. For example, fluid from an external fluid supply unit may be supplied to the mouth cavity proper 32 through the second tubular member 308, the first anchoring member 302, and the first tubular member 306 in that order. Fluid within the mouth cavity proper 32 can be removed to an external fluid recovery unit through the first tubular member 306, the second anchoring member 304, and the third tubular member 310. In various aspects, the third tubular member 310 can be sized and configured to allow a desired flow rate of the fluid to be removed. For example, the third tubular member 310 can have a larger passage than the first and second tubular members 306 and 308 where the fluid to be removed has a viscosity that is greater than a viscosity of the fluids to be delivered.

Figure 12:
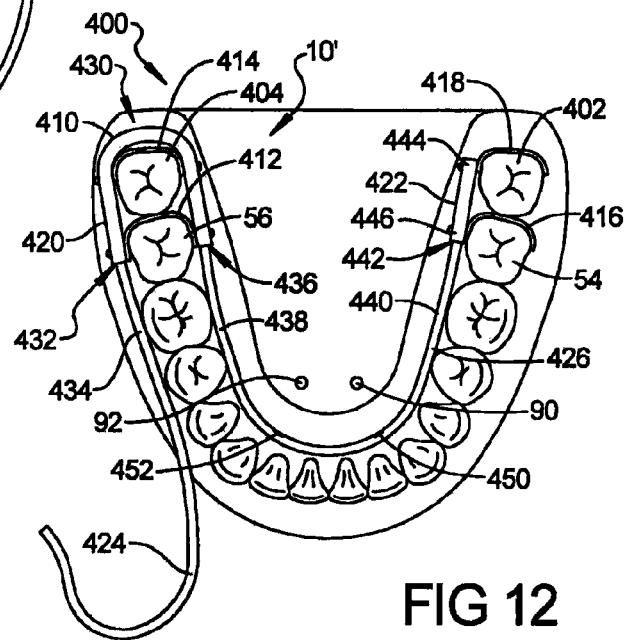
FIG. 12 is an environmental top elevation view of a lower portion of a mouth illustrating another exemplary mouthpiece according to the present disclosure.

With particular reference to FIG. 12, an environmental top elevation view of a mouth 10' illustrates another mouthpiece 400 according to the present disclosure. The mouth 10' is substantially similar to the mouth 10, except that the mouth 10' includes two additional molars 402, 404. The mouthpiece 400 can include a tube assembly 410 and anchoring members 412, 414, 416, 418. The tube assembly 410 can be adapted to transfer fluid between a first location in the mouth cavity proper 32 and a second location outside of the mouth 10'. For example, the tube assembly 410 can supply fluid from a fluid supply unit located outside the mouth 10' to the mouth cavity proper 32. As another example, the tube assembly 410 can be used to remove excess fluid within the mouth cavity proper to a fluid recovery unit located outside the mouth 10'.

The tube assembly 402 can include a first tubular member 420, a second tubular member 422, a flexible first tube 424, and a flexible second tube 426. The first tubular member 420 can be adapted to provide fluid communication between the first and second tubes 424 and 426 and to pass through a space 430 adjacent a rearmost tooth. The first tubular member 420 can be further adapted to support the first and second tubes 424 and 426. According to the present example, the first tubular member 420 can be a rigid U-shaped tube that extends from the vestibule 34, around the molar 404 through the space 430, and to the mouth cavity proper 32.

The first tubular member 420 can include a first opening 432 at a first end adapted to receive an end 434 of the first tube 424 in a press-fit arrangement. The first tubular member 420 can include a second opening 436 at a second end opposite the first end that receives an end 438 of the second tube 424 in a press-fit arrangement. The first tubular member 420 can be attached to the mouth 10' in any suitable manner. For example, the first tubular member 420 can be attached to one or more of the lower teeth 20. According to the present example, the first tubular member 420 can attach to the molars 56 and 404 via the anchoring members 412 and 414, respectively. The first tubular member 420 can cooperate with the anchoring members 412, 414 to support the ends 434 and 438 of the first and second tubes 424 and 426 at a desired orientation or angle.

The second tubular member 422 can be adapted to seal an end 440 of the second tube 426 and can be further adapted to support the end 440 within the mouth 10'. The second tubular member 422 can be an elongated rigid cylindrical cap that includes a first open end 442, a second closed end 444, and a longitudinal passage 446 at a desired orientation or angle. The longitudinal passage 446 can extend through the open end 442 towards the closed end 444 and can be adapted to receive the end 440 of the second tube 426 in a press-fit arrangement. The second tubular member 422 can be attached to the mouth 10' in any suitable manner. For example, the second tubular member 422 can be attached to one or more teeth in a manner similar to that of the first tubular member 420. According to the present example, the second tubular member 422 can attach to the molars 54 and 402 via the anchoring members 416 and 418, respectively. The second tubular member 422 can cooperate with the anchoring members 416 and 418 to support the end 440 of the second tube 426 within the mouth 10' at a desired orientation or angle with respect to the openings 90, 92 of the submandibular duct.

The first tube 424 can be a length of flexible tubing adapted to couple to the first tubular member 420 and to transport fluid between the first tubular member and a desired location outside of the mouth 10'. The first tube 424 can extend through the vestibule 34 and can be sized to provide a desired fluid flow.

The second tube 426 can be a length of transparent flexible tubing adapted to couple to the first and second tubular members 420 and 422. The second tube 426 can be further adapted to extend along the inner gum line 80 at a desired orientation with respect to the tongue and the openings 90, 92 of the submandibular duct and to retain a desired shape. The second tube 426 can be substantially similar to the first tubular member 104 and can include apertures 450 and 452 disposed along the length so as to be located near the openings 90, 92 of the submandibular duct. In this way, the apertures 450, 452 can direct fluid towards an area where saliva excreted through the openings 90, 92 would normally collect.

The anchoring members 412 and 414 can be adapted to attach the first tubular member 420 to the molars 56 and 404, respectively. The anchoring members 416 and 418 can be adapted to attach the second tubular member 422 to the molars 54, 402. In various aspects, the anchoring members 412, 414 can have a substantially similar configuration. Accordingly, the anchoring member 412 will be described in further detail with the understanding that the description can apply equally to the anchoring member 414.

Figure 13:
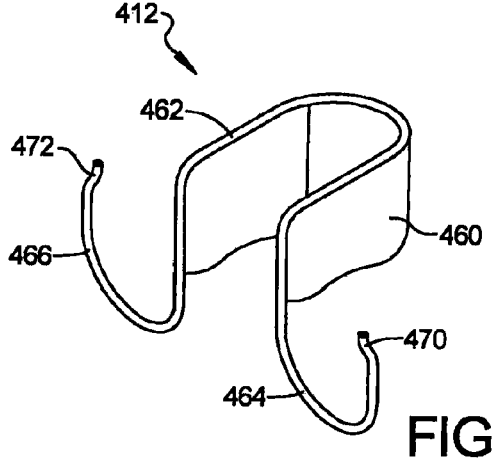
FIG. 13 is a perspective view illustrating an exemplary anchoring member of the mouthpiece shown in FIG. 12.

With particular reference to FIG. 13, a perspective view illustrates an exemplary configuration of the anchoring member 412. The anchoring member 412 can include a cap 460 and a clip member 462. The cap 460 can be adapted to engage the crown 66 of the molar 56 in a close fit and to support the clip member 462 on the molar 56. The cap 460 can be formed of a thin material, such as a metal, and can have a contour complementary to the crown 66 of the molar 56. The clip member 462 can be attached to the cap 460 and can be adapted to releasably retain the tube assembly 410 and, more particularly, the first tubular member 420. The clip member 462 can include U-shaped clips 464 and 466 having inwardly turned ends 470 and 472, respectively, which can releasably retain respective portions of the first tubular member 420 in a snap-fit arrangement.

The anchoring members 416, 418 can have a substantially similar configuration and the configuration can be similar to that of the anchoring members 412, 414. For example, the anchoring members 416, 418 can include a cap and a clip member substantially similar to the cap 460 and the clip member 462 described above, except that the clip member can include a single clip that releasably retains the second tubular member 422.

In various aspects, the mouthpiece 400 can be configured with an additional tube similar to the mouthpiece 300. For example, the mouthpiece 400 can include a second tubular member substantially similar to the first tubular member that attaches to the molars 54, 402 via anchoring members similar to the anchoring members 412, 414. The second tube can be coupled to an end of the second tubular member disposed in the mouth cavity proper 32 and a third tube can be coupled to an opposite end of the second tubular member disposed in the vestibule 34. The third tube can extend from the second tubular member to a location outside of the mouth.

Figure 14:
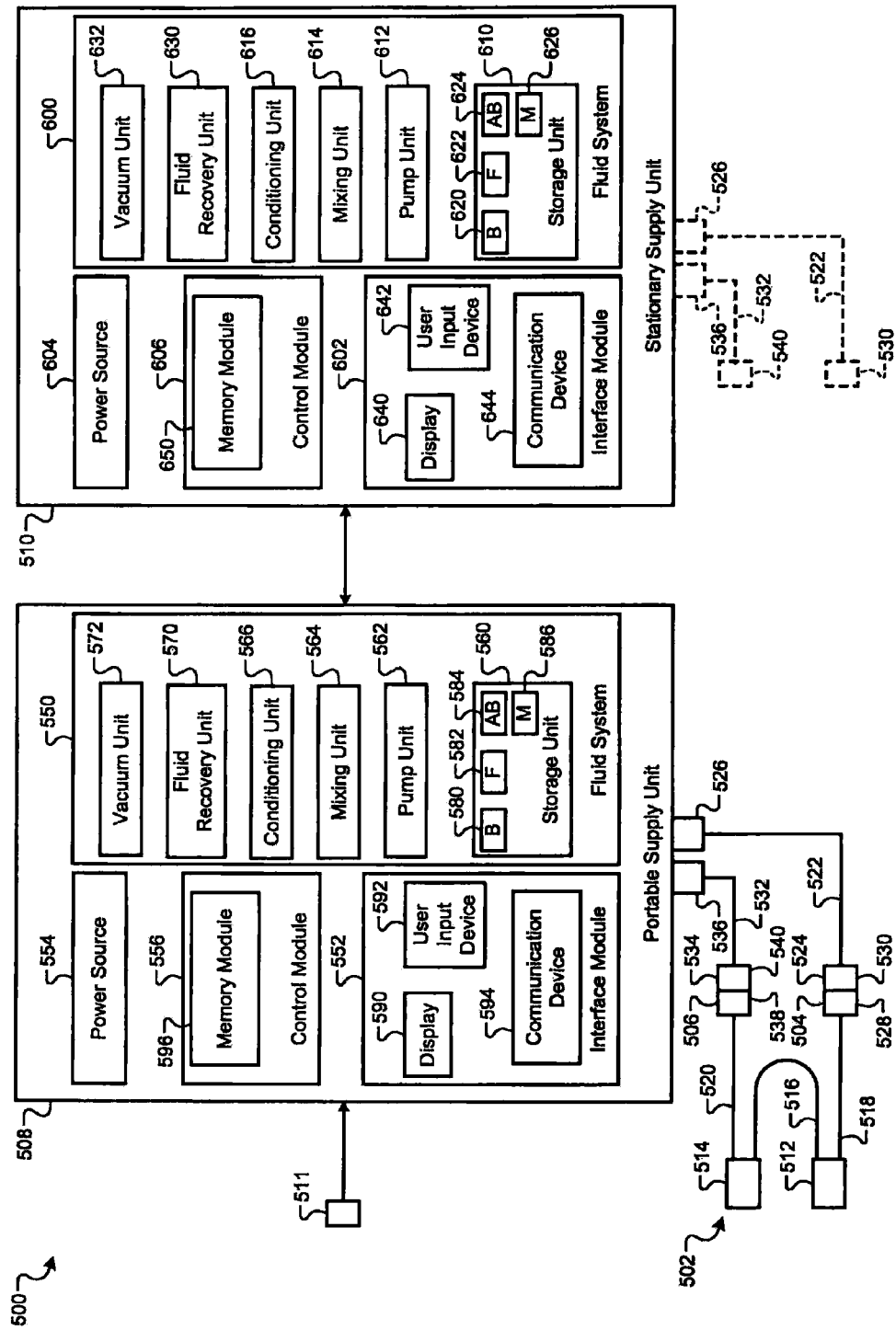
FIG. 14 is a functional block diagram illustrating an exemplary system according to the present disclosure.

With particular reference to FIG. 14, a functional block diagram illustrates an exemplary system 500 according to the present disclosure. The system 500 can include a mouthpiece 502, fluid couplings 504, 506, a portable supply unit 508, and a stationary supply unit 510. The system 500 can further include a moisture sensor 511 that senses a moisture content of the mouth and outputs a signal indicative of the moisture content sensed. In various aspects, the moisture sensor 511 can be attached to the mouthpiece 502 and can be formed integral with a component of the mouthpiece 502 as a single part. Alternatively, the moisture sensor 511 can be attached to a separate location within the mouth.

The mouthpiece 502 can be a mouthpiece according to the present disclosure such as one of the mouthpieces 12, 300, 400. For exemplary purposes, the mouthpiece 502 presented can be substantially similar to the mouthpiece 300 and can include a first anchoring member 512, a second anchoring member 514, a first tubular member 516, a second tubular member 518, and a third tubular member 520. The first anchoring member 512, the second anchoring member 514, the first tubular member 516, the second tubular member 518, and the third tubular member 520 can be substantially similar to the first anchoring member 302, the second anchoring member 304, the first tubular member 306, the second tubular member 308, and the third tubular member 310, respectively.

The fluid coupling 504 can couple the second tubular member 518 to the portable supply unit 508 or the stationary supply unit 510 as desired. The fluid coupling 504 can include a tube 522 and fluid connectors 524, 526 disposed at opposite ends of the tube 522. The fluid connector 524 can include a first connector 528 that couples to the second tubular member 518 and a second connector 530 complementary to the first connector 528 that couples to the tube 522. The first and second connectors 528 and 530 can provide a detachable fluid connection between the mouthpiece 502 and the fluid coupling 504. The fluid connector 526 can provide a detachable fluid connection between the fluid coupling 504 and the portable supply unit 508 and the stationary supply unit 510.

The fluid coupling 506 can couple the third tubular member 310 to the portable supply unit 508 or the stationary supply unit 510 as desired. The fluid coupling 506 can include a tube 532 and fluid connectors 534, 536 disposed at opposite ends of the tube 532. The connector 534 can include a first connector 538 that couples to the third tubular member 520 and a second connector 540 complementary to the first connector 538 that couples to the tube 532. The first and second connectors 438 and 540 can provide a detachable fluid connection between the mouthpiece 502 and the fluid coupling 506. The fluid connector 536 can provide a detachable fluid connection between the fluid coupling 506 and the portable supply unit 508 and the stationary supply unit 510.

Figure 15A:
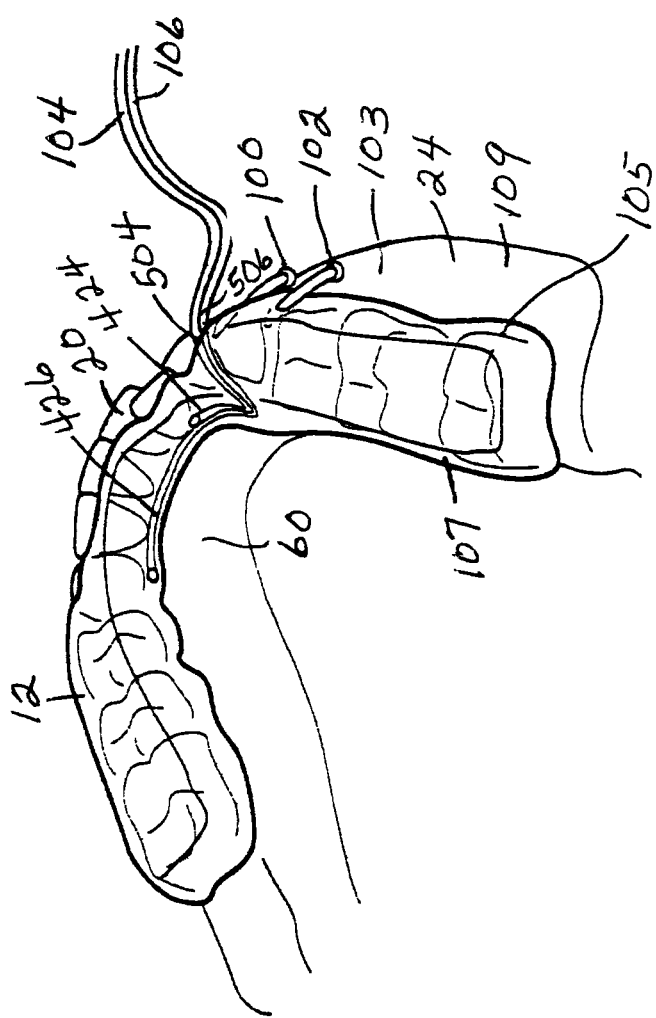
FIGS. 15a-15c represent perspective views of the mouthpiece according to the present teachings.
Figure 15B:
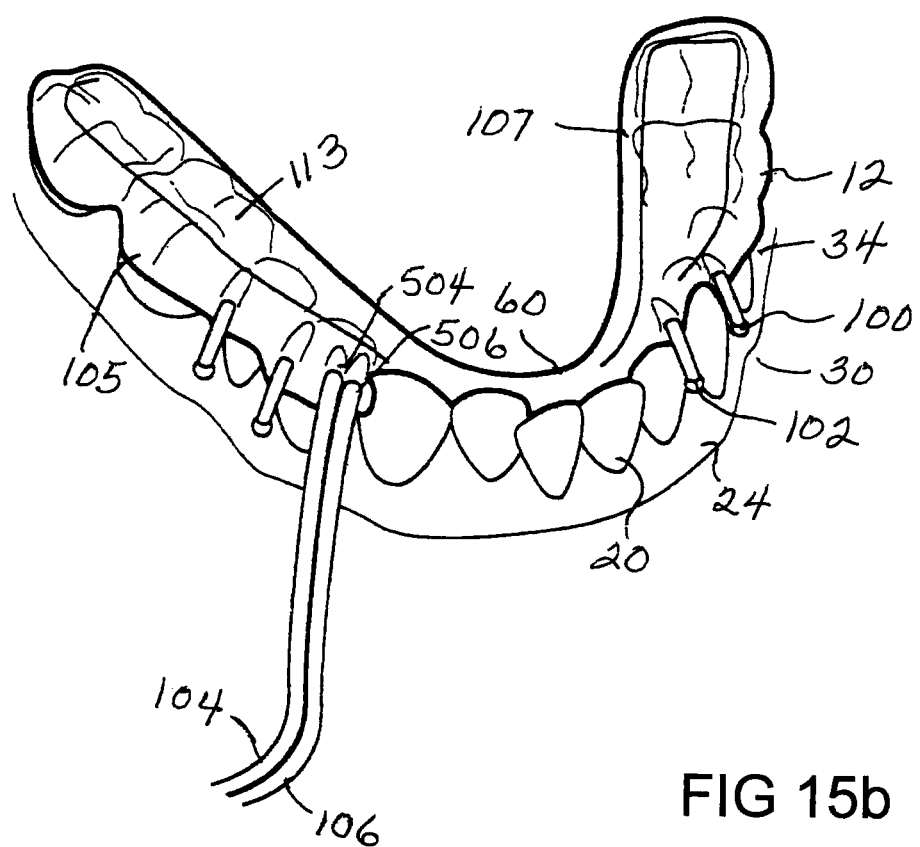
Figure 15C:
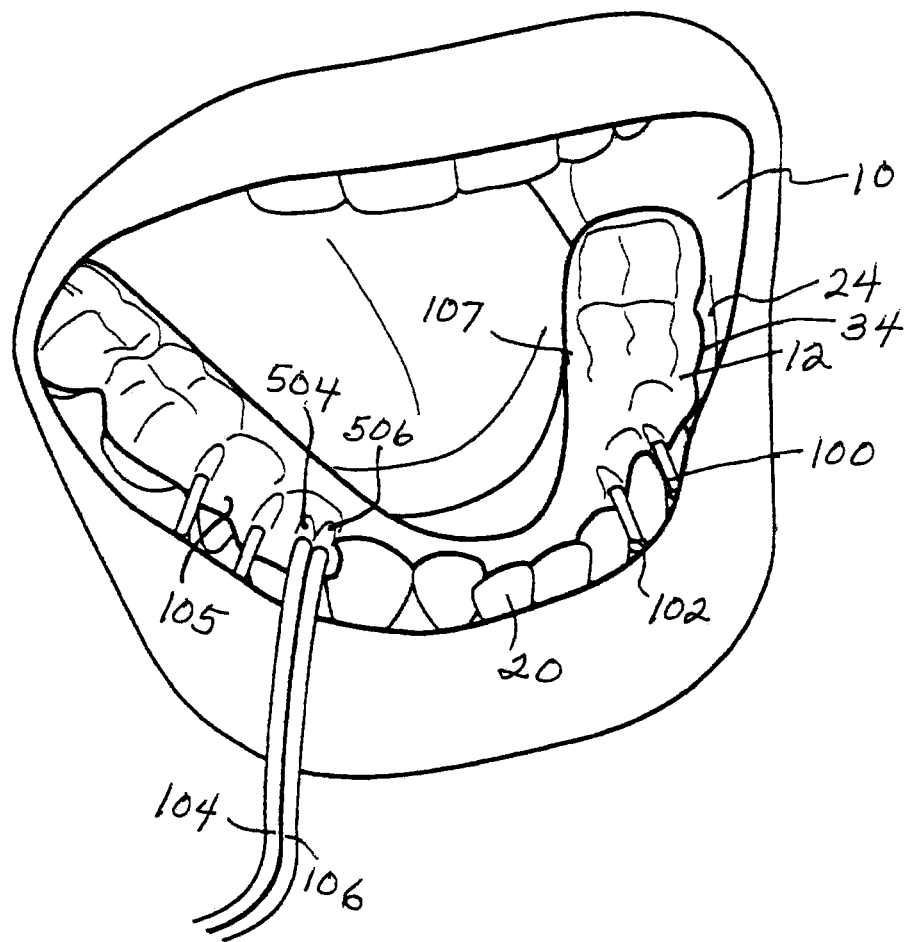
Figure 16:
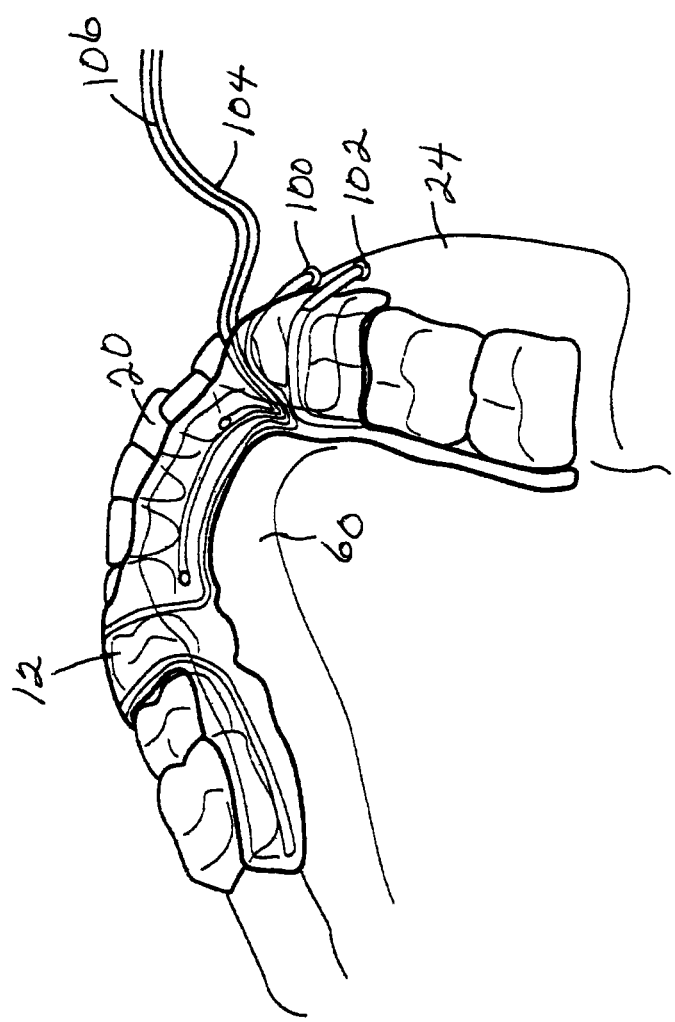
FIG. 16 represents a perspective view of an alternate mouthpiece according to the present teachings.
Figure 17A:
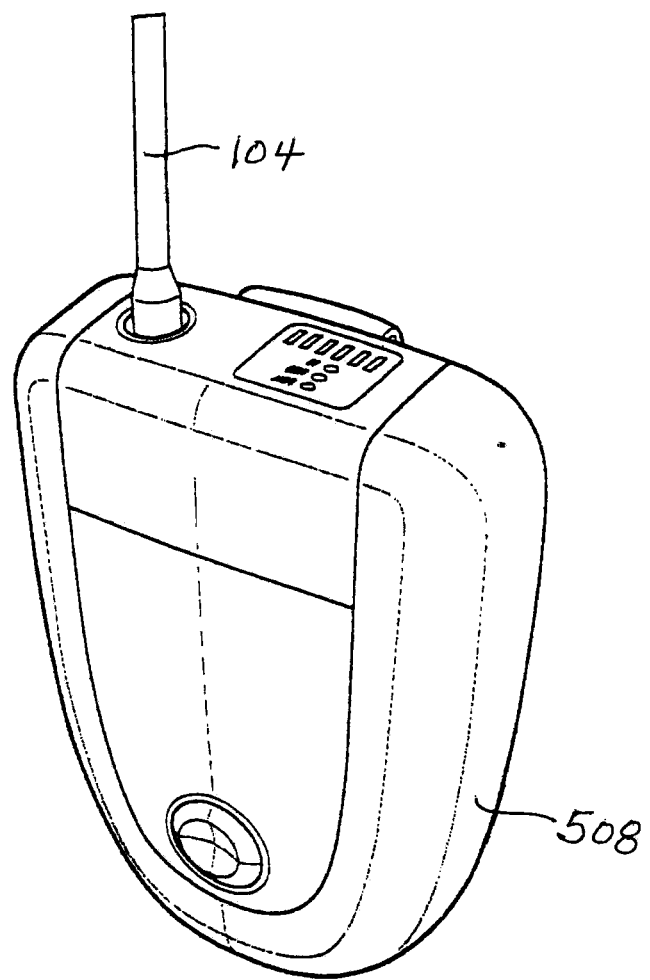
FIGS. 17a-20b represent fluid supplies according to the present teachings.
Figure 17B:
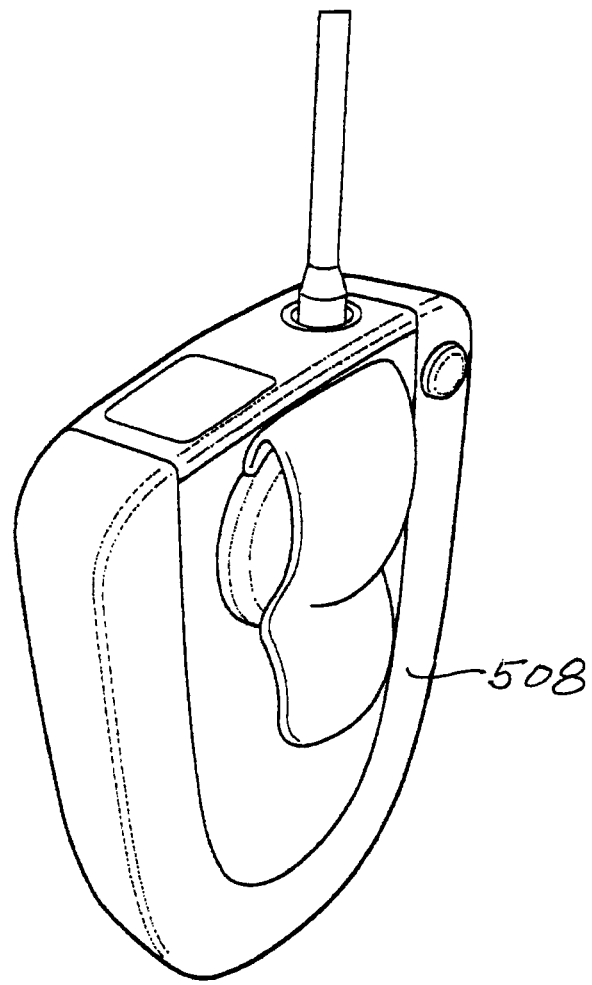
Figure 18:
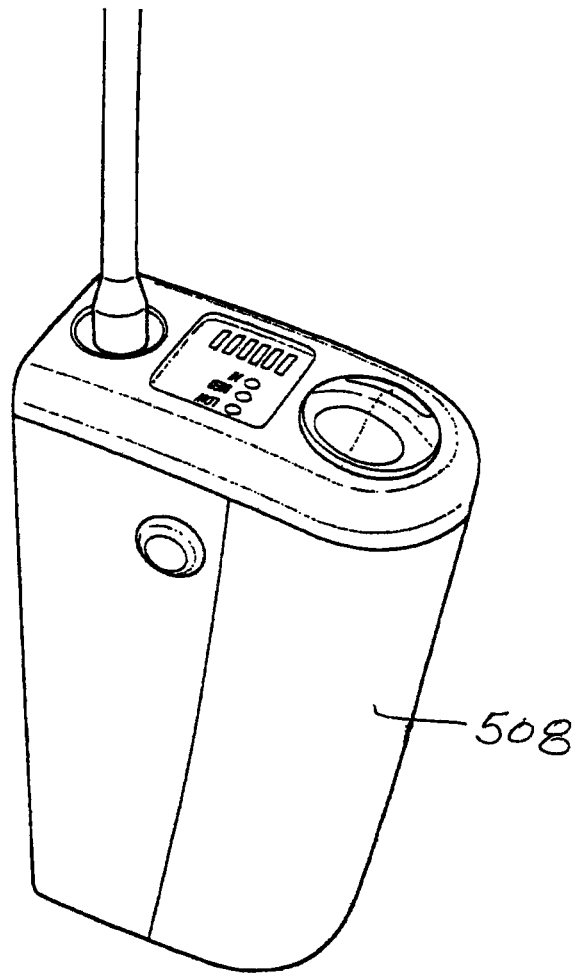
Figure 19:
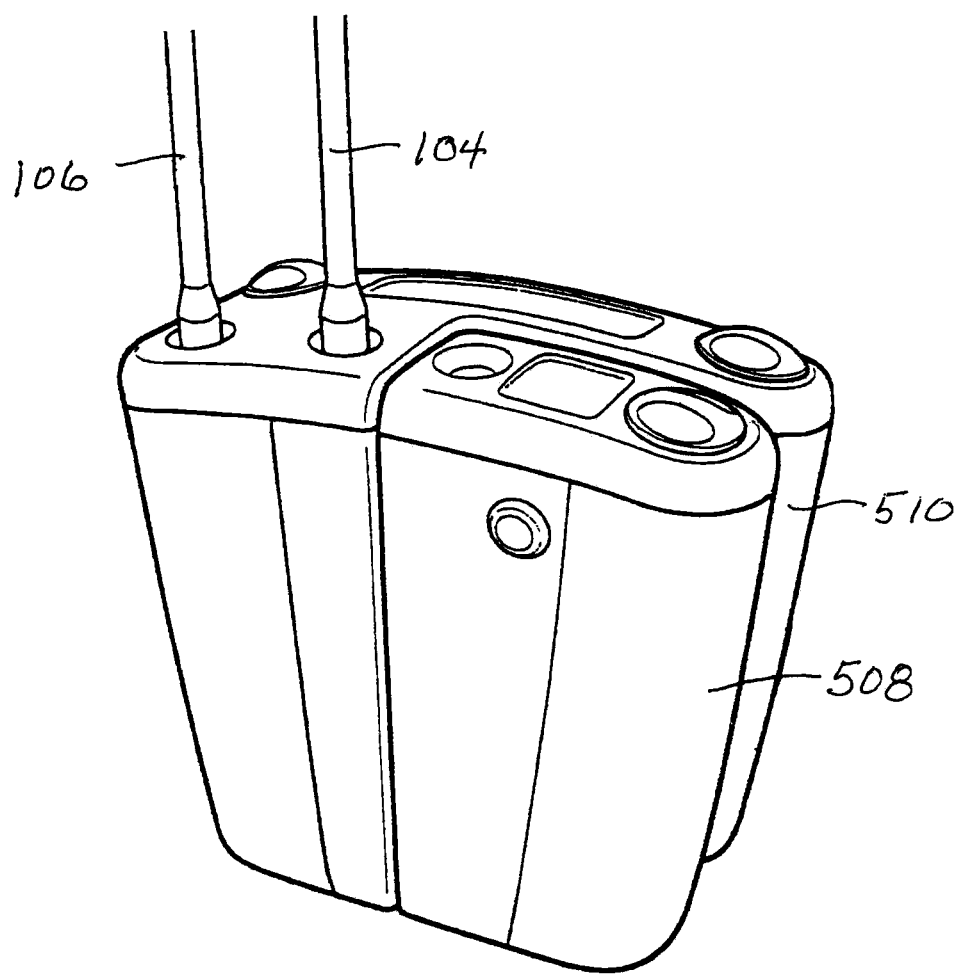
Figure 20A:
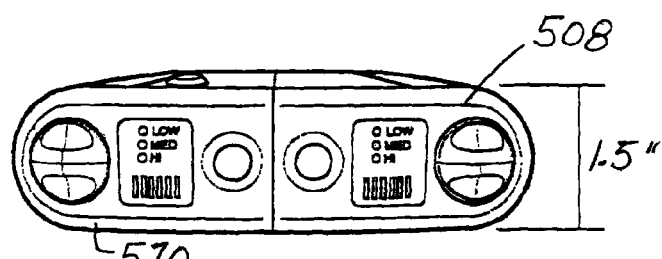
Figure 20B:
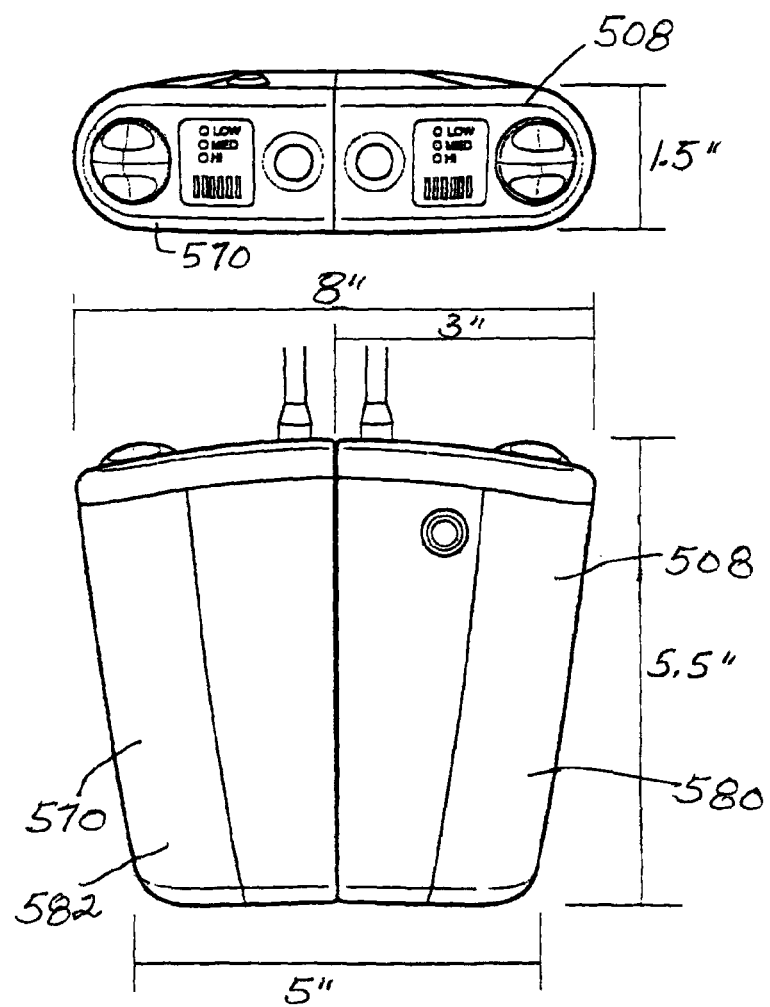

As seen in FIGS. 15a-20b, generally, the portable supply unit 508 can be worn by a user and thereby carried as the user moves about. The portable supply unit 508 can be used daily to control saliva replenishment and removal from a mouth of the user whose salivary production is compromised. As shown in FIG. 17, the portable supply unit 508 can be suitably lightweight so as to be comfortably worn by the user throughout the day. The portable supply unit 508 can be adapted to be clipped onto a belt and/or carried in a pocket. The portable supply unit 508 can be battery operated. In various aspects, the portable supply unit 508 can be insulated for suitably quiet operation. The portable supply unit 508 can have an aesthetically pleasing appearance (e.g., fashionable design) in contrast to that typical of a medical device. In this way, the appearance of the portable supply unit 508 can reduce any perceived stigma associated with wearing the portable supply unit 508 out in public. When used with children, the portable supply unit 508 can include features similar to popular cartoon characters and, optionally can be placed inside a stuffed animal cover or casing.

The portable supply unit 508 can supply saliva replenishment fluid to the mouth and remove excess fluids from the mouth via the mouthpiece 502. The portable supply unit 508 can further be configured to dock with the stationary supply unit 510. The portable supply unit 508 can include a fluid system 550, an interface module 552, a power source 554, and a control module 556. The fluid system 550 can include a supply system including a storage unit 560, a pump unit 562, a mixing unit 564, and a conditioning unit 566. The fluid system 550 can further include a recovery system including a fluid recovery unit 570, and a vacuum unit 572.

The storage unit 560 can store a predetermined quantity of the saliva replenishment fluid. The quantity can correspond to, for example, an estimated usage in a single day. In various aspects, the saliva replenishment fluid can include a base agent, a flavored agent, an antibacterial agent, medications, and/or supplemental vitamins. The base agent can be a primary component of the saliva replenishment fluid that functions similar to natural saliva. Accordingly, the base agent can include various compounds including, but not limited to, water, electrolytes, anti-bacterial compounds, and enzymes. The flavored agent can be a sour agent that stimulates or activates the salivary glands and natural saliva production. Sour agents may be particularly useful for patients undergoing radiation treatments affecting saliva production. For example, stimulating natural saliva production can help flush out radiation residue that may cause damage if present in the mouth for prolonged periods. The anti-bacterial agent can be the same or a different anti-bacterial compound present in the base agent. The anti-bacterial agent can work together with the base agent to further inhibit bacteria within the mouth and within the various components of the system 500 that carry the saliva replenishment fluid. Together, the anti-bacterial agent and the base agent can also help preserve the proper flora in the mouth and improve mouth hygiene. The medications can include one or more medicaments used to treat the mouth of the user and/or to provide other unrelated therapeutic benefits to the user. For example, the medicaments can be oral medications that would otherwise have to be administered by the user or a health care professional. As another example, the medicaments can include a numbing agent. As yet another example, the medicaments can include fluoride-containing compounds used to prevent tooth decay or otherwise promote oral hygiene.

The storage unit 560 can include one or more reservoirs that store components of the saliva replenishment fluid. For example, the storage unit 560 can include a reservoir 580 that stores the base agent, a reservoir 582 that stores the flavored agent, a reservoir 584 that stores the anti-bacterial agent, and a reservoir 586 that stores the medications and/or the supplemental vitamins. In various aspects, the storage unit 560 can provide access to the reservoirs 580, 582, 584, 586. In this way, fluid containers can be carried separately by the user and can be used to easily pour replacement fluids into the respective reservoirs 580, 582, 584, 586. In other aspects, the reservoirs 580, 582, 584, 586 can be compartments that receive pre-mixed bags containing associated fluids. In still other aspects, the reservoirs 580, 582, 584, 586 can be removed individually or together to enable cleaning.

The pump unit 562 can draw the various components of the saliva replenishment fluid from the storage unit 560 and supply the components to the mixing unit 564 under pressure at a desired rate. In various aspects, the pump unit 562 can include pumps individually coupled to the reservoirs 580, 582, 584, 586. In this way, the pump unit 562 can individually supply the various components in varying amounts as desired.

The mixing unit 564 can mix the pressurized fluids received from the pump unit 562 and supply the mixed fluids to the conditioning unit 566.

The conditioning unit 566 can heat and/or cool the mixed fluids received from the mixing unit 564 to a predetermined temperature and can provide the conditioned fluids to the coupling 504.

The fluid recovery unit 570 can store fluid removed from the mouth by the vacuum unit 572 in a suitable manner until the fluid is removed from the portable supply unit 508 and disposed of in a suitable manner.

The vacuum unit 572 can be coupled to the mouthpiece 502 via the fluid coupling 506. The vacuum unit 572 can create a vacuum that draws excess fluid within the mouth into the first tubular member 516 and to the fluid recovery unit 570 via the second anchoring member 514, the third tubular member 520, and the fluid coupling 506. In various aspects, the fluid recovery unit 570 and/or the vacuum unit 572 can be part of a separate device that is attachable to the portable supply unit 508. In this way, the portable supply unit 508 can be made smaller and the units can be selectively used.

The interface module 552 can provide an interface for exchanging information between the portable supply unit 508 and the stationary supply unit 510 and the user. The interface module 552 include a display 590, a user input device 592, and a communication device 594. The display 590 can display various information including, but not limited to user information, an operating mode, a program, fluid delivery settings, fluid removal settings, reservoir levels within the storage unit 560, a fluid level within the fluid recovery unit 570. The display 640 can include a visual display and audible chimes for conveying information.

The user input device 592 can enable a user to enter data and user information, and change various system operating parameters including the operating mode, the program, and the fluid delivery and removal settings.

The communication device 594 can communicate various information between the portable supply unit 508 and the stationary supply unit 510. The communication device 594 can further communicate various information between other designated devices such as a personal computer, a network computer, or a cellular phone. In this way, the communication device 594 can exchange information and synchronize operation of the portable supply unit 508 and the stationary supply unit 510. The communication device 594 can communicate via wired and/or wireless communication methods. In various aspects, communication can be initiated by the communication device 594, a user input, and/or docking of the portable supply unit 508 with the stationary supply unit 510.

The power source 554 can supply power used to operate the portable supply unit 508. The power source 554 can include rechargeable batteries. The batteries can be recharged by an external power source and/or optionally by the stationary supply unit 510. In various aspects, recharging may be initiated when the portable supply unit 508 is plugged in to the external power source and/or is docked with the stationary supply unit 510.

The control module 556 can control operation of the portable supply unit 508 based on various inputs. The inputs can include, but are not limited to, inputs received via the interface module 552 and the moisture content communicated in the signal output by the moisture sensor 511. More specifically, the control module 556 can control the delivery rate of the saliva replenishment fluid and the removal rate of fluid from the mouth. The control module 556 can further control communication between the portable supply unit 508 and the stationary supply unit 510. In various aspects, the control module 556 can execute predetermined programs for controlling operation. The programs can be designed to meet specific saliva production requirements for a particular user, users afflicted with similar conditions, various states of consciousness, and the like.

The programs can be further designed to allow adjustments to settings such as a delivery rate of the saliva replenishment fluid, a removal rate of fluid from the mouth, and manual operation by the user. For example, the programs can include a program for automatically controlling operation during periods when the user is awake and a program for automatically controlling operation when the user is asleep. In various aspects, these automatic programs can account for differences in an amount of saliva replenishment fluid required, dosing related to any medicaments, and required delivery rates of the various fluids contained in the storage unit 560. For example, less saliva replenishment fluid may be required while the user is asleep.

The programs can further include a program enabling manual operation by the user. The programs can further include a program for executing a flushing operation during which the pump unit 562 and the vacuum unit 572 cooperate to pass saliva replenishment fluid from the storage unit 560 to the fluid recovery unit 570 and thereby flush the passages between them. The programs can further include a program that executes a hydration operation during which a quantity of saliva replenishment fluid can be supplied and a portion can be subsequently removed at regular intervals. The hydration operation can be used to hydrate the mouth of a user who has lost the ability to swallow.

The control module 556 can include a memory module 596. The memory module 596 can include volatile and nonvolatile memory where the various programs, control parameters, and settings according to the present disclosure are stored.

Generally, the stationary supply unit 510 can be placed in a location where a user spends prolonged periods. For example, the location may be near a bed, a chair, or other resting place.

In various aspects, the stationary supply unit 510 can be adapted to rest on a horizontal surface of, for example, a night stand or end table, or to attach to a vertical surface of, for example, a wall. The stationary supply unit 510 can have a functionality similar to that of the portable supply unit 508, yet can be larger than the portable supply unit 508 in order to contain a larger supply of saliva replenishment fluid, store a larger quantity of fluid removed from the mouth, provide a larger display, and/or provide larger or additional user input devices. For example, the stationary supply unit 510 can contain a quantity of saliva replenishment fluid corresponding to one or more days of estimated usage. The stationary supply unit 510 can include a plug adapted to receive power from a standard electrical outlet and can optionally include a battery backup system that supplies power when power from the electrical outlet is interrupted. The stationary supply unit 510 can be insulated for suitably quiet operation and can be designed to have an aesthetically pleasing appearance. Quiet operation and good aesthetics can help ensure patient compliance with therapies associated with the system 500.

The stationary supply unit 510 can supply saliva replenishment fluid to the mouth and remove excess fluids from the mouth via the mouthpiece 502. The stationary supply unit 510 can include a fluid system 600, an interface module 602, a power source 604, and a control module 606. In various aspects, the fluid system 600 can be substantially similar to the fluid system 550, except that the fluid system 600 can be adapted to store larger quantities of saliva replenishment fluid and fluid removed from the mouth. Accordingly, the fluid system 600 can include a supply system including a storage unit 610, a pump unit 612, a mixing unit 614, and a conditioning unit 616. The storage unit 610 can include reservoirs 620, 622, 624, 626 similar to, yet larger than the reservoirs 580, 582, 584, 586. The pump unit 612, the mixing unit 614, and the conditioning unit 616 can be substantially similar to the pump unit 562, the mixing unit 564, and the conditioning unit 566, respectively.

The fluid system 600 can further include a recovery system including a fluid recovery unit 630, a vacuum unit 632. The fluid recovery unit 630 can be similar to the fluid recovery unit 570, except that the fluid recovery unit 630 can be adapted to contain a larger quantity of fluid removed from the mouth. The vacuum unit 632 can be substantially similar to the vacuum unit 572.

The interface module 602 can provide an interface for exchanging information between the stationary supply unit 510 and the portable supply unit 508 and the user. The interface module 602 can include a display 640, a user input device 642, and a communication device 644. The display 640 can include a visual display and audible chimes for conveying the information. The user input device 642 can include buttons, keys, and other suitable devices that enable the user to input information and manually control operation of the stationary supply unit 510. The communication device 644 can communicate various information between the stationary supply unit 510 and the portable supply unit 508, and other designated devices as desired. The communication device 644 can communicate via wired and/or wireless communication methods.

The power source 604 can include rechargeable batteries that supply power when external power is not available. The power source 604 can also be configured to recharge the batteries of the portable supply unit 508 when docked.

The control module 606 can control operation of the stationary supply unit 510 based on various inputs including, but not limited to, inputs received via the interface module 602 and from the moisture sensor 511. More specifically, the control module 606 can control the delivery rate of the saliva replenishment fluid and the removal rate of fluid from the mouth. The control module 606 can further control communication between the stationary supply unit 510, the portable supply unit 508, and other designated devices. In various aspects, the control module 606 can execute predetermined programs for controlling operation. The programs can include programs similar to those executed by the portable supply unit. Accordingly, the programs can include a program for automatically controlling operation during periods when the user is awake, a program for automatically controlling operation when the user is asleep, a program enabling manual operation by the user, and a program for executing a flushing operation.

The control module 556 can include a memory module 650. The memory module 650 can include volatile and non-volatile memory where the various programs, control parameters, and settings according to the present disclosure are stored.

With continued reference to FIG. 14, a method of using the system 500 will be described. The method can include coupling the mouthpiece 502 to the portable supply unit 508 during periods when the user is mobile or desires mobility, and to the stationary supply unit 510 during periods when the user is stationary. The method can further include communicating information between the portable supply unit 508 and the stationary supply unit 510. The method can further include communicating information between one of the portable supply unit 508 and the stationary supply unit 510 and a separate designated device.

FIGS. 15a-15c represent perspective views of the mouthpiece 12 according to another teaching of the present disclosure. The mouthpiece 12 is configured to be placed over and engaged with teeth associated with the lower dental arch 103. The mouthpiece 12 has first and second coupling members 105, 107. The first coupling member is configured to be adjacent to an outer side 109 of the dental arch 103. The second coupling member 107 is configured to conform to and engage an inner side 111 of the dental arch 103.

As shown in FIGS. 15a-15c, the mouthpiece 12 has a coupling member 113 which covers the teeth. The coupling member 113 defines a pair of through bores 424 and 426. These through bores 424 and 426 function to supply fluid and vacuum in the mouth. Also shown is a pair of coupling anchoring members 100 and 102 which couple the mouthpiece 12 to the dental arch 103.

As shown in FIG. 16, the mouthpiece can be custom formed about a patient's lower (or upper) dental arch. The mouthpiece can cover only a portion of the biting surface of the teeth, leaving a portion exposed for chewing. Additionally, the mouthpiece can have a thickness over a forward portion of the biting surface of between 1.5 and 9 mm and preferably less than 6.4 mm and most preferably less than 2 mm, so as to minimally interfere with the users normal biting and chewing profile. As shown, the mouthpiece 12 can have an extended flange which internally covers a larger portion of the inner surface of the dental arch. As shown, the coupling anchoring members 100 and 102 can be extended wires integrally molded into the polymer material defining the mouthpiece 12.

FIGS. 17a-20b represent fluid sources 508 according to the present teachings. These fluid sources have power sources 554, control module 559, interface module 552 and fluid handling system 550 as described above. The fluid handling system can have the vacuum unit 572, fluid recovery unit 570, conditioning unit 566, mixing unit 564 and pump 562. Additionally, the fluid source can have an emergency shutoff that functions to turn off the pump, unit 562 or vacuum unit 572 under an undesirable operating condition.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It is additionally envisioned the systems described above can be used in conjunction with a positive airflow sleep apnea machine. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. A system for regulating fluid in a mouth cavity of a user, the mouth cavity having a dental arch with a biting surface and vestibule on an outer side of the dental arch, and a gum line on the dental arch, the system comprising:
    a mouthpiece having a coupling member configured to couple the mouthpiece to the dental arch, the mouthpiece having a first tube member configured to be adjacent the outer side of the dental arch, the mouthpiece defining a first fluid passage through a portion of the first tube member and further a plurality of passages fluidly coupled to the first fluid passage and located adjacent the gum line, the coupling member covering only a portion of the molar region of the biting surface;
    a fluid conduit coupled to the first fluid passages; and
    a supply source of vacuum coupled to the first fluid passage.

2. The system according to claim 1, wherein the mouthpiece comprises first and second anchoring members adapted to engage the dental arch.

3. The system according to claim 2, wherein the first anchoring member is configured to engage the gum line.

4. The system according to claim 2, wherein the control unit is configured to regulate a vacuum level.

5. The system according to claim 1, wherein the supply source of vacuum comprises a pump and a controller configured to regulate the amount of vacuum through the first fluid passage.

6. The system according to claim 5, wherein the supply source of vacuum further comprises fluid collection container coupled to the first fluid passage.

7. The system according to claim 6, wherein the controller is configured to control the amount of vacuum applied to the first passage.

8. A system for regulating fluid in a mouth cavity of a user, the mouth cavity having a dental arch with a biting surface and a vestibule on an outer side of the dental arch, and a gum line of the dental arch and at least one tooth, the system comprising:
    a mouthpiece having a first tube member configured to engage the outside of the dental arch and defining a first fluid passage there through and a plurality of suction passages adjacent the gum line, the mouthpiece further having a second member configured to engage the inner side of the dental arch, a coupling member disposed between the first and second members, the coupling member defining a second through fluid passage, said mouthpiece having first and second anchoring members adapted to engage only a portion of the molar region of the biting surface adjacent the tooth; and
    a vacuum supply coupled to the first through fluid passage.

9. The system according to claim 8, wherein the vacuum supply has a controller configured to apply a vacuum to the first through passage to remove fluid from the mouth.

10. The system according to claim 8, wherein the vacuum supply further comprises a controller configured to regulate a pump coupled to the vacuum supply.

11. The system according to claim 8, further comprising a conduit disposed between the mouthpiece and the vacuum supply.

12. The system according to claim 11, wherein the mouthpiece comprises a first quick fluid coupling disposed between the conduit and the mouthpiece.

13. A system for regulating fluid in a mouth cavity of a user, the mouth cavity having a lower dental arch with a biting surface and a vestibule on an outer side of the lower dental arch, a plurality of teeth, and a gum line of the dental arch, the system comprising:

a mouthpiece having a first tube member defining a first through fluid passage and a plurality of suction orifices fluidly coupled to the first fluid through passage and positions adjacent the gum line, the first tube member being configured to engage the outside of the dental arch and a member configured to engage the inner side of the dental arch, a pair of coupling members covering only a portion of a molar region of the biting surface and disposed between the first tube member and the member, the coupling member conforming to a portion of the teeth and defining a second fluid passage, said mouthpiece having first and second anchoring members each being adapted to selectively couple the first and second anchoring members to the dental arch;

a vacuum supply fluidly coupled to the second through fluid passage;

a conduit fluidly disposed between and fluidly coupling the vacuum supply to the first fluid passage; and a controller configured to regulate the flow of fluid from the mouthpiece.

14. The system according to claim 13, wherein the first anchoring member is a deformable wire.

15. The system according to claim 14, wherein the mouthpiece comprises a first quick fluid coupling disposed between the conduit and the mouthpiece.

16. The system according to claim 13, wherein the controller is coupled to a vacuum, and configured to apply a vacuum to the second through passage to remove fluid from the mouth.

17. The system according to claim 13, wherein the controller is configured to regulate a pump coupled to the mouthpiece.

* * * * *